US012618095B2

(12) United States Patent
Koyanagi

(10) Patent No.: US 12,618,095 B2
(45) Date of Patent: May 5, 2026

(54) **MEDIUM FOR *BACILLUS CEREUS* GROUP DETECTION**

(71) Applicant: SHIMADZU DIAGNOSTICS CORPORATION, Tokyo (JP)

(72) Inventor: Yusuke Koyanagi, Yuki (JP)

(73) Assignee: SHIMADZU DIAGNOSTICS CORPORATION, Tokyo (JP)

( * ) Notice: Subject to any disclaimer, the term of this patent is extended or adjusted under 35 U.S.C. 154(b) by 661 days.

(21) Appl. No.: 17/907,617

(22) PCT Filed: Mar. 30, 2021

(86) PCT No.: PCT/JP2021/013502

§ 371 (c)(1),
(2) Date: Sep. 28, 2022

(87) PCT Pub. No.: WO2021/200927

PCT Pub. Date: Oct. 7, 2021

(65) Prior Publication Data

US 2023/0143236 A1 May 11, 2023

(30) Foreign Application Priority Data

Mar. 31, 2020 (JP) ................................. 2020-064835

(51) Int. Cl.
*C12Q 1/04* (2006.01)
(52) U.S. Cl.
CPC .............. *C12Q 1/04* (2013.01); *C12Q 1/045* (2013.01)
(58) Field of Classification Search
None
See application file for complete search history.

(56) References Cited

U.S. PATENT DOCUMENTS

| | | | |
|---|---|---|---|
| 6,284,517 B1 | 9/2001 | Restaino | |
| 6,558,917 B2 * | 5/2003 | Schabert | ................ C12Q 1/045 435/4 |
| 2003/0032080 A1 | 2/2003 | Schabert | |
| 2004/0005652 A1 | 1/2004 | Restaino | |
| 2015/0176052 A1 | 6/2015 | Cellier et al. | |
| 2016/0319326 A1 | 11/2016 | Cellier et al. | |
| 2016/0319362 A1 | 11/2016 | Ruminy et al. | |

FOREIGN PATENT DOCUMENTS

| | | |
|---|---|---|
| CN | 101215597 A | 7/2008 |
| CN | 104480186 A | 4/2015 |
| CN | 106811403 A | 6/2017 |
| JP | 2005-525825 A | 9/2005 |
| JP | 2011-4712 A | 1/2011 |
| KR | 10-2012-0048862 A | 5/2012 |

OTHER PUBLICATIONS

International Search Report issued May 11, 2021 in PCT/JP2021/013502 filed on Mar. 30, 2021, 3 pages.
"Standard Methods of Analysis in Food Safety Regulation", Microorganisms 2004, under the supervision of Ministry of Health, Labour and Welfare, incorporated association Japan Food Hygiene Association, pp. 266-282 (with partial unedited computer-generated English translation).
ISO 11133 "Microbiology of food, animal feed and water-Preparation, production, storage and performance testing of culture media", Amendment 2 (2014), 17 pages.
ISO 7932 "Microbiology of food and animal feeding stuffs-Horizontal method for the enumeration of presumptive *Bacillus cereus*—Colony-count technique at 30° C.", (2004), 31 pages.
Fricker et al., "Evaluation of standard and new chromogenic selective plating media for isolation and identification of *Bacillus cereus*", International Journal of Food Microbiology, 2008, vol. 121, [2], pp. 27-34.
Extended European Search Report issued Apr. 23, 2024, in corresponding European Patent Application No. 21779068.2, 6 pages.
Combined Chinese Office Action and Search Report issued Apr. 28, 2024 in Chinese Patent Application No. 202180021985.4 (with unedited computer-generated English Translation of Office Action only), 11 pages.
Japanese Office Action issued May 7, 2025, in corresponding Japanese Patent Application No. 2022-512282 (with English Translation), 13 pages.

* cited by examiner

*Primary Examiner* — Vera Afremova
(74) *Attorney, Agent, or Firm* — Oblon, McClelland, Maier & Neustadt, L.L.P.

(57) ABSTRACT

A medium for *Bacillus cereus* group detection, which is favorable in growth of *Bacillus cereus* regardless of the temperature condition, and further is excellent in selectivity; and a method for detecting a *Bacillus cereus* group using the medium. The medium for *Bacillus cereus* group detection includes a phosphatidylinositol-specific phospholipase C substrate having a detectable chromogenic or fluorescent free radical; and trimethoprim. The medium further includes a β-lactam antibiotic. The medium further includes an antifungal agent. The method for detecting further includes inoculating a sample into the medium to culture the sample; and determining a detectable colony on the medium.

3 Claims, 2 Drawing Sheets

MEDIUM FOR *BACILLUS CEREUS* GROUP DETECTION

CROSS REFERENCE TO RELATED APPLICATIONS

This application is a National Stage entry under 35 U.S.C. § 371 of PCT/JP2021/013502, filed on Mar. 30, 2021, and claims priority to Japanese Patent Application No. 2020-064835, filed on Mar. 31, 2020, the entire contents of which are incorporated herein by reference.

FIELD OF THE INVENTION

The present invention relates to a medium for *Bacillus cereus* group detection.

BACKGROUND OF THE INVENTION

*Bacillus cereus* is a gram-positive spore-forming *bacillus*, and in general, is widely distributed in the natural world such as soil and rivers. The range of contamination by the present bacterium is a broad range starting from, for example, grains and spices, which are foods having a close relationship with soil, to, for example, food products that are cross-contaminated by using such foods, for example, noodles such as chow mein, and spaghetti, cooked rice such as rice balls, and fried rice, gratin, pizza, fish and shellfish, processed products of fish and shellfish, meat, processed products of meat, a food raw material, confectionery, environment, and a clinical material.

Contamination with the present bacterium sometimes causes rotting and deterioration. Further, the present bacterium is known to produce a vomiting toxin and a diarrhea toxin, and may cause food poisoning.

Therefore, the control of the present bacterium is important also from the viewpoint of food hygiene and safety (Non Patent Literature 1).

In general, as the medium used for detecting *Bacillus cereus*, for example, a NGKG (Nacl-Glycine-Kim-Goepfect) agar medium, and a MYP (Mannitol Yolk-Polymixin) agar medium (for example, Non Patent Literatures 1 to 3) are known. These media contain egg yolk in order to utilize egg yolk reaction that is one of the characteristics of *Bacillus cereus*, as one of the detection principles. The method for preparing the egg yolk-containing medium includes a step of sterilizing and dissolving a medium raw material such as agar other than egg yolk in advance, a step of cooling and keeping the dissolved material at around 50° C., a step of further aseptically adding and mixing collected egg yolk to the material, and a step of aliquoting the medium raw material mixed in this way into a Petri dish and solidifying the medium raw material.

As described above, at least three steps are required when adding egg yolk, and the procedure is complicated. This is to prevent thermal denaturation of the egg yolk component, and in particular, in the cooling and keeping step, if the medium temperature in the addition of the collected egg yolk is extremely high, the egg yolk component is denatured, while if the medium temperature is extremely low, for example, solidification of the agar is caused, and thus, it is important to control the temperature, and a skilled experience is required. In addition, since the state of the collected egg yolk used in the detection principle largely and easily varies depending on, for example, the species, the individual difference, and the breeding environment, of a hen for egg collection, the medium performance is affected by the state of the collected egg yolk, and thus, it is required to have an empirical rule for discrimination of a colony having the egg yolk reaction after culture.

In view of this, the present applicant has reported a medium containing four components of polymyxin B, trimethoprim, a lincomycin antibiotic, and 5-bromo-4-chloro-3-indoxyl-$\alpha$-D-glucopyranoside to be a substrate of $\alpha$-glucosidase, as the medium for *Bacillus cereus* group detection, which does not use egg yolk reaction (Patent Literature 1).

Further, a medium for selective detection of *Bacillus cereus* and *Bacillus thuringiensis*, obtained by mixing, for example, lithium chloride, ceftazidime, polymixin B sulfate, in addition to a phosphatidylinositol-specific phospholipase C substrate having a detectable chromogenic or fluorescent free radical, and nutrient components has been reported (Patent Literature 2).

CITATION LIST

Patent Literature

Patent Literature 1: JP 2011-004712 A
Patent Literature 2: U.S. Pat. No. 6,284,517

Non Patent Literature

Non Patent Literature 1: Standard Methods of Analysis in Food Safety Regulation, Microorganisms 2004, under the supervision of Ministry of Health, Labour and Welfare, incorporated association JAPAN FOOD HYGIENE ASSOCIATION, pages 266 to 282
Non Patent Literature 2: ISO11133 Microbiology of food, animal feed and water-Preparation, production, storage and performance testing of culture media (2014)
Non Patent Literature 3: ISO7932 Microbiology of food and animal feeding stuffs—Horizontal method for the enumeration of presumptive *Bacillus cereus*—Colony-count technique at 30° C. (2004)

SUMMARY OF THE INVENTION

Technical Problem

However, it has been found that as to the medium disclosed in Patent Literature 1, there may be a case where a clear detection of colony cannot be done because the growth of *Bacillus cereus* is insufficient in 24 hours under the condition of 30° C. that is similar to the culture condition of a MYP medium of ISO7932, and there is a problem of, for example, false positive in some parts of the genus *Staphylococcus*. In addition, it has been found that in the medium disclosed in Patent Literature 2, not only the *Bacillus cereus* group but also, for example, the *Listeria monocytogenes* results in positive.

Accordingly, an object of the present invention is to provide a medium for *Bacillus cereus* group detection, which can be easily produced, is favorable in growth of *Bacillus cereus* regardless of the temperature condition, and further is excellent in selectivity, and to provide a method for detecting a *Bacillus cereus* group using the medium.

Solution to Problem

In view of the above circumstances, as a result of various studies on the medium specialized for detecting a *Bacillus cereus* group and the method for detecting the *Bacillus*

*cereus* group, the present inventors found that by using a phosphatidylinositol-specific phospholipase C substrate having a detectable chromogenic or fluorescent free radical as a chromogenic or fluorescent substrate, and by containing trimethoprim in a medium, the growth of a *Bacillus cereus* group can be improved while inhibiting the growth of microorganisms other than the *Bacillus cereus* group without using egg yolk reaction, and thus completed the present invention.

That is, the present invention is to provide the following inventions [1] to [7].

[1] A medium for *Bacillus cereus* group detection, including: a phosphatidylinositol-specific phospholipase C substrate having a detectable chromogenic or fluorescent free radical; and trimethoprim.

[2] The medium for *Bacillus cereus* group detection disclosed in [1], further including a β-lactam antibiotic.

[3] The medium for *Bacillus cereus* group detection described in [1] or [2], further including an antifungal agent.

[4] The medium for *Bacillus cereus* group detection described in any one of [1] to [3], in which the phosphatidylinositol-specific phospholipase C substrate having a detectable chromogenic or fluorescent free radical is selected from the group consisting of 5-bromo-4-chloro-3-indoxyl myo-inositol-1-phosphate, 5-bromo-6-chloro indoxyl myo-inositol-1-phosphate, 6-chloro-3-indoxyl myo-inositol-1-phosphate, 4-methylumbelliferone myo-inositol 1-phosphate, 4-nitrophenyl-myo-inositol-1-phosphate, luciferin-myo-inositol-1-phosphate, and a salt thereof.

[5] The medium for *Bacillus cereus* group detection described in any one of [2] to [4], in which the β-lactam antibiotic is selected from the group consisting of a penicillin antibiotic, a cephem antibiotic, a carbapenem antibiotic, a monobactam antibiotic, and a penem antibiotic.

[6] The medium for *Bacillus cereus* group detection described in any one of [1] to [5], in which the *Bacillus cereus* group is a bacterium selected from the group consisting of *Bacillus cereus, Bacillus anthracis, Bacillus thuringiensis, Bacillus mycoides, Bacillus pseudomycoides, Bacillus weihenstephanensis, Bacillus cytotoxicus*, and *Bacillus toyonensis*.

[7] A method for detecting a *Bacillus cereus* group, including: inoculating a sample into the medium described in any one of [1] to [6] to culture the sample; and determining a detectable colony on the medium.

Advantageous Effects of the Invention

By using the medium for *Bacillus cereus* group detection of the present invention, the presence of a *Bacillus cereus* group in a specimen in which various microorganisms are mixed can be accurately efficiently and easily discriminated, and further, the medium is inexpensive, and is simply and easily prepared. Therefore, the medium of the present invention can be widely used for inspection of, for example, general foods and beverages, and water, and for inspection of production process.

DESCRIPTION OF EMBODIMENTS

Figure 1:
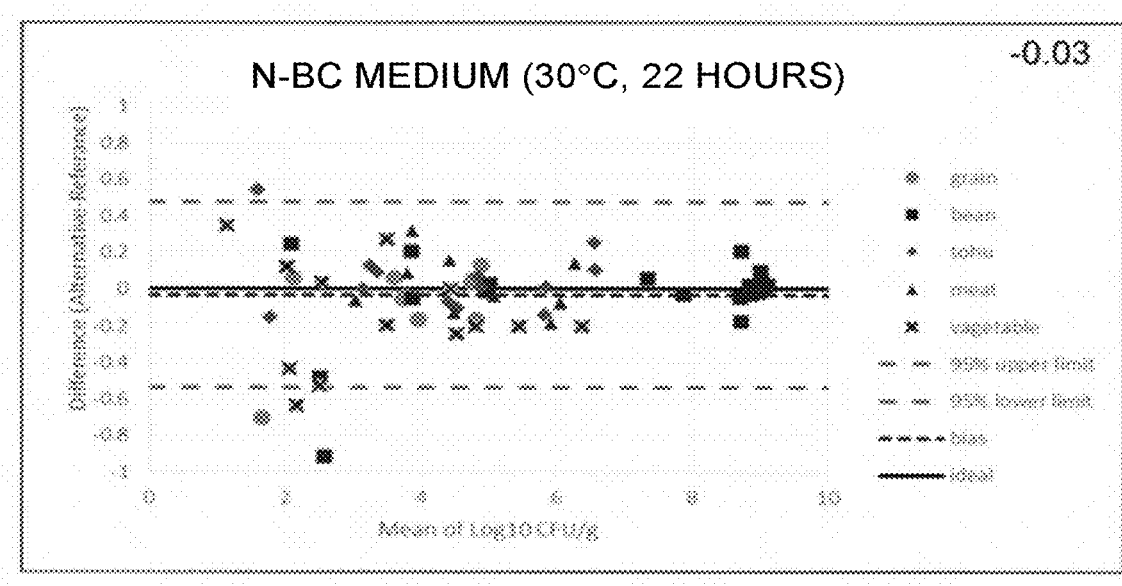
FIG. 1 is a diagram in which the growth abilities of an N-BC medium and an EX-BC medium are each compared with the growth ability of a MYP medium as the basis by using a sample inoculated with *B. cereus* as a food sample.
Figure 1:
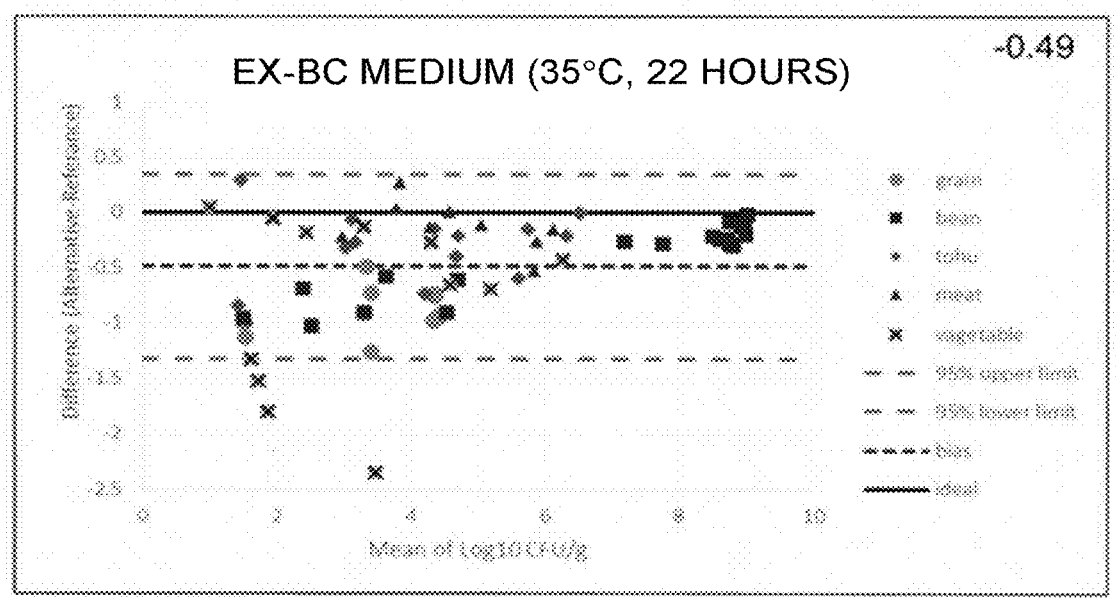

The *Bacillus cereus* group to be subjected to the detection according to the present invention includes *Bacillus cereus*, and a bacterium that is genetically close to and has biochemical properties similar to those of the *Bacillus cereus*. Examples of the bacterium in the *Bacillus cereus* group include bacteria selected from *Bacillus cereus, Bacillus anthracis, Bacillus thuringiensis, Bacillus mycoides, Bacillus pseudomycoides, Bacillus weihenstephanensis, Bacillus cytotoxicus*, and *Bacillus toyonensis*. Among them, the present invention is preferably used for detection of *Bacillus cereus, Bacillus thuringiensis, Bacillus mycoides*, and *Bacillus weihenstephanensis*, and more preferably used for detection of *Bacillus cereus*, and *Bacillus thuringiensis*.

In the medium of the present invention, as the chromogenic or fluorescent substrate, a phosphatidylinositol-specific phospholipase C substrate having a detectable chromogenic or fluorescent free radical is used. The substrate is decomposed by phosphatidylinositol-specific phospholipase C (PI-PLC) produced by *Bacillus cereus* that is subjected to the detection of the present invention, and the detectable chromogenic or fluorescent free radical is released.

Examples of the chromogenic or fluorescent substrate of PI-PLC include 5-bromo-4-chloro-3-indoxyl myo-inositol phosphate, 5-bromo-6-chloro-3-indoxyl myo-inositol phosphate, 6-chloro-3-indoxyl myo-inositol-1-phosphate, 4-methylumbelliferone myo-inositol 1-phosphate, 4-nitrophenyl-myo-inositol-1-phosphate, luciferin-myo-inositol-1-phosphate, and a salt thereof. Among them, 5-bromo-4-chloro-3-indoxyl myo-inositol-1-phosphate (hereinafter, may also be referred to as X-IP) is particularly preferable in terms of the color development, and the ease of differentiation of colonies.

In the present invention, by using a chromogenic or fluorescent substrate of PI-PLC as the chromogenic substrate, a colony of a *Bacillus cereus* group can be clearly differentiated regardless of the temperature condition, without inhibiting the growth of the *Bacillus cereus* group, only by trimethoprim as a growth inhibitor for microorganisms other than the *Bacillus cereus* group (hereinafter, also referred to as "other microorganisms"). Therefore, it is advantageous in that there is no need to add polymyxin B and lincomycin, which are required in Patent Literature 1.

From the viewpoint of favorable color development and determination, the content of the chromogenic or fluorescent substrate of PI-PLC in a medium is preferably 0.001 to 10 g/L, more preferably 0.01 to 5 g/L, and furthermore preferably 0.1 to 1 g/L, as the concentration at the time of detection.

The trimethoprim used in the medium of the present invention acts as a growth-inhibiting substance for other microorganisms. By the addition of trimethoprim, the growth of Gram-positive bacteria (particularly, the genus *Staphylococcus*, and the genus *Enterococcus*) and Gram-negative bacteria, other than the many representative *Bacillus cereus* group can be inhibited. In particular, the trimethoprim has a strong inhibitory effect on the growth of Gram-negative bacteria and also acts on Gram-positive bacteria other than the *Bacillus cereus* group.

Specific examples of the trimethoprim include trimethoprim, and a lactate thereof.

The content of trimethoprim in a medium is not particularly limited, but is preferably 0.01 to 500 mg/L, more preferably 0.1 to 50 mg/L, and furthermore preferably 1 to 5 mg/L, as the concentration at the time of detection.

In the medium of the present invention, it is preferable to contain a β-lactam antibiotic in addition to the above two components for the purpose of enhancing the growth inhibition of Gram-negative bacteria. As the β-lactam antibiotic, one or two or more kinds selected from a penicillin antibiotic, a cephem antibiotic, a carbapenem antibiotic, a monobactam antibiotic, and a penem antibiotic are used. Among them, from the viewpoint of enhancing the growth inhibition of Gram-negative bacteria, a cephem antibiotic, or a monobactam antibiotic is more preferable.

Examples of the cephem antibiotic include third-generation cephalosporins, for example, ceftriaxone, cefotaxime, ceftizoxime, ceftazidime, cefoperazone, cefsulodin, ceftibuten, and cefetamet. Further, examples of the monobactam antibiotic include aztreonam, tigemonam, carumonam, nocardicin, and tabtoxin. Among them, ceftazidime or aztreonam is preferably used. The content of the β-lactam antibiotic in a medium is preferably 0.001 to 100 mg/L, more preferably 0.01 to 25 mg/L, and furthermore preferably 0.5 to 5 mg/L, as the concentration at the time of detection.

In addition, it is preferable to contain further an antifungal agent in the medium of the present invention. As the antifungal agent, one kind or two or more kinds selected from a polyene antifungal agent (for example, amphotericin B), a candin antifungal agent (for example, micafungin, or caspofungin), an azole antifungal agent (for example, fluconazole, voriconazole, or itraconazole), an allylamine antifungal agent (for example, terbinafine), and a fluoropyrimidine antifungal agent (for example, flucytosine) are used. Among them, it is preferable to contain amphotericin B for the purpose of suppressing the growth of fungi. The concentration of the antifungal agent in a medium is not particularly limited, but is preferably 0.001 to 100 mg/L, more preferably 0.1 to 10 mg/L, and furthermore preferably 1 to 5 mg/L, as the concentration at the time of detection.

Further, it is preferable to contain a sugar alcohol and/or an inorganic salt in the medium of the present invention.

In this regard, examples of the sugar alcohol include sugar alcohols of a monosaccharide and an oligosaccharide, such as erythritol, xylitol, sorbitol, mannitol, and maltitol. Among them, it is preferable to use mannitol because the differentiation of a *Bacillus cereus* group becomes easy. These may be used alone, or by mixing two or more kinds thereof.

The content of the sugar alcohol in a medium is not particularly limited, but is preferably 1 to 50 g/L, more preferably 5 to 30 g/L, and particularly preferably 5 to 20 g/L, as the concentration at the time of detection.

In addition, examples of the inorganic salt include an inorganic acid metal salt such as sodium chloride, or sodium thiosulfate; and an organic acid metal salt such as ferric ammonium citrate, or sodium citrate. Among them, the inorganic acid metal salt is preferable, and particularly, sodium chloride is preferable because the differentiation of a *Bacillus cereus* group becomes easy. These may be used alone, or by mixing two or more kinds thereof.

The content of the inorganic salt in a medium is not particularly limited, but is preferably 0.1 to 20 g/L, more preferably 1 to 10 g/L, and particularly preferably 3 to 8 g/L, as the concentration at the time of detection.

In addition to the above medium components, the medium of the present invention may contain cell nutrient components such as a carbon source, a nitrogen source, a mineral, and a vitamin, and a medium component such as a pH adjusting agent.

Examples of the carbon source include one or more kinds selected from, for example, glucose, fructose, lactose, and saccharose; examples of the nitrogen source include one or more kinds selected from, for example, a protein degradation product (such as casein peptone, soy peptone, or meat peptone), a yeast extract, a meat extract, and a fish extract; examples of the mineral source include one or more kinds selected from, for example, copper, zinc, magnesium, and cobalt; and examples of the vitamin include one or more kinds selected from, for example, nicotinic acid, pantothenate, biotin, riboflavin, and folic acid.

Further, examples of the component used for a pH adjusting agent include an organic acid salt of oxalic acid, acetic acid, fumaric acid, malic acid, lactic acid, gluconic acid, or tartaric acid; an inorganic salt of phosphoric acid, hydrochloric acid, or sulfuric acid; a carbonate such as sodium carbonate, or sodium hydrogen carbonate; a hydroxide such as sodium hydroxide; ammonia or ammonia water; an amine citrate; a lower alkanolamine; a basic amino acid such as arginine, or lysine. These may be used alone, or by mixing two or more kinds thereof. In this case, the pH of a medium may be adjusted so as to be preferably 5 to 8, more preferably 6.5 to 7.7, and furthermore preferably 6.8 to 7.4.

In addition, in order to obtain a solid or semi-solid medium, the medium of the present invention may contain a solidifying component or a gelling component, for example, a naturally-derived component such as gelatin, agar, xanthane gum, locust bean gum, guar gum, or carrageenan, or a synthetic origin component such as hydroxyethyl cellulose. These may be used alone, or by mixing two or more kinds thereof.

Further, a liquid medium is allowed to be absorbed in the medium of the present invention by using a fibrous liquid-absorbing material such as a fibrous water-absorbent sheet, and the obtained medium may be used as a simple medium. Examples of the fibers include natural fibers derived from a plant or an animal, and chemical fibers derived from, for example, chemical synthesis or glass fibers, and a nonwoven fabric obtained by forming fibers into a sheet shape is preferable.

Examples of the simple medium include simple media prepared by preparation methods disclosed in JP S57-502200 A, JP H03-015379 A, JP H02-065798 A, JP H06-181741 A, JP H09-019282 A, and JP 2000-325072 A.

As one specific example of the simple medium, for example, a simple medium obtained by supporting a medium composition containing (a) an adhesive agent soluble both in water and alcohol, (b) a gelling agent soluble in water and insoluble in alcohol, and (c) cell nutrient components on a fibrous water absorbent sheet having a mesh larger than the gelling agent (JP H09-019282 A), or a simple culture medium produced by impregnating a fibrous water-absorbent sheet with a suspension formed by suspending in an alcohol (a) an adhesive (0.01-0.4 wt %) which is soluble both in water and alcohol, (b) a gelling agent which is soluble in water and insoluble in alcohol, and (c) a bacterial nutritive ingredient, the fibrous water-absorbent sheet having a mesh larger than the particle size of the gelling agent and being placed on a waterproof flat plate, and by drying the resultant sheet while controlling rapid evaporation of the alcohol, to thereby cause the water-absorbent sheet to adhere onto the waterproof flat plate (JP 2000-325072 A) can be mentioned.

Examples of the above adhesive soluble both in water and alcohol include hydroxypropyl cellulose, and polyvinyl pyrrolidone. Further, examples of the above gelling agent soluble in water and insoluble in alcohol include ones mentioned in the above solidifying component or gelling component. The average particle size of the gelling agent is preferably 0.5 to 50 μm.

Examples of the form of the medium of the present invention are not particularly limited, but include a liquid medium, an agar medium, and a sheet-shaped simple medium. Examples of the preparation method in that case include a method in which for example, purified water is added in each of the above medium composition components, the mixture is mixed and stirred, and then the resultant mixture is sterilized in, for example, an autoclave, the sterilized mixture is aliquoted into, for example, a sterilized Petri dish, and the mixture in the dish is cooled or allowed to cool down (at this time, heat-sensitive components such as an enzyme substrate, and an antibiotic may be added separately after the autoclave sterilization and before the aliquoting); and a method in which for example, alcohol, or purified water is added in each of the above medium components, the mixture is mixed and stirred, and then the resultant mixture is aliquoted into a container (for example, plastic, or glass) storing a fibrous liquid-absorbing material, and sterilized with gamma irradiation. Examples of the alcohol include ethanol, and 2-propanol.

In the method for detecting a *Bacillus cereus* group of the present invention, a sample is inoculated into the above-obtained medium for detection and cultured under predetermined conditions, and then a detectable colony on the medium is determined.

In this regard, the expression "detectable colony" refers to a formed colony having a specific color tone that can be confirmed visually or in the presence of fluorescence, and by differentiating the colony, the presence of a *Bacillus cereus* group is determined.

As the sample, although it is not particularly limited, for example, a food suspension, an environmental sample wiped from a kitchen or a cooking tool, a culture solution cultured in a medium for enrichment, a soil suspension, river water, or drinking water is used.

This sample may be inoculated as it is or after being concentrated or diluted into the medium of the present invention, and cultured. At this moment, it is preferable to concentrate or dilute the sample around 10 to $10^{-10}$ times when inoculating the sample, from the viewpoint of the measurement of the number of colonies.

Further, as the inoculation method, although it is not particularly limited, a flat-plate smear method, a streak smearing method, or a membrane filter method (method in which a filter after filtering a sample is placed on a medium and the sample is cultured) is preferable.

The culture temperature is not particularly limited, but it is preferable to be 10 to 48° C., and particularly 30 to 35° C., at which a *Bacillus cereus* group can grow. Further, the culture time is not particularly limited, but it is preferable to be 18 to 48 hours, and particularly 22 to 26 hours. It is preferable that the culture is performed aerobically while being left to stand.

As to the color or fluorescence of the colony (including the surroundings) of a *Bacillus cereus* group formed in a medium, since an enzyme substrate that develops color or emits fluorescence is used in the present invention, a colony of a *Bacillus cereus* group is differentiated by the presence of color development or fluorescence of the substrate, but meanwhile, in a case where the presence of such a color tone or fluorescence is not observed, such a case is determined not to be a colony of a *Bacillus cereus* group. In particular, in a case where X-IP is used as the enzyme substrate, the determination is performed by the change in color tone of blue. As described above, the presence or absence of a *Bacillus cereus* group or the number of colonies is determined in a sample.

EXAMPLES

Hereinafter, the present invention will be specifically described with reference to Examples, however, the present invention is not limited to the following Examples.

Test Example 1: Agar Medium

[Preparation of Medium]

A medium composition based on a standard methods agar (SMA) medium is shown in Table 1, and a medium composition based on a Trypticase soy agar (TSA) medium is shown in Table 2.

Preparation method: The medium (SMA-BC) of the present invention based on the SMA and the medium (TSA-BC) of the present invention based on the TSA were prepared as follows. In a mixture of the medium composition (excluding X-IP) of Table 1 or Table 2, 1 L of purified water was added, the mixture was dissolved in the purified water while heating at 121° C. for 15 minutes, and the obtained mixture was thoroughly stirred, then into the mixture, X-IP was added, and the resultant mixture was stirred and aliquoted in a plastic Petri dish (90Φ mm) by 20 mL at a time, and the mixture in the dish was left to stand until being solidified.

[Strain Under Test]

*B. cereus* ATCC11778 was precultured for 24 hours in TSA, the precultured *B. cereus* ATCC11778 was adjusted by using a 0.86% sterilized NaCl solution (sterilized saline solution) so that a bacterial liquid at $1\times10^2$ to $1\times10^6$ cfu/mL was obtained, and the bacterial liquid was inoculated into respective media by 0.05 mL each.

[Culture Results]

As shown in Table 3, when each strain was subjected to a test and cultured at 30° C. for 22 hours, favorable growth and development of blue color of *B. cereus* were observed in the SMA-BC and the TSA-BC.

From the results, it was found that by combining a phosphatidylinositol-specific phospholipase C substrate having a detectable chromogenic free radical, such as X-IP with trimethoprim, the *Bacillus cereus* can be detected.

TABLE 1

| No. | Raw material name | Composition |
|-----|-------------------|-------------|
| 1 | Casein peptone | 5.0 g |
| 2 | Yeast extract | 2.5 g |
| 3 | Glucose | 1.0 g |
| 4 | Agar | 15.0 g |
| 5 | X-IP | 0.6 g |
| 6 | Trimethoprim | 0.005 g |

TABLE 2

| No. | Raw material name | Composition |
|---|---|---|
| 1 | Peptone | 15.0 g |
| 2 | Soy peptone | 5.0 g |
| 3 | Sodium chloride | 5.0 g |
| 4 | Agar | 15.0 g |
| 5 | X-IP | 0.6 g |
| 6 | Trimethoprim | 0.005 g |

TABLE 3

| Bacterium | | | Adjusted bacterial concentration | | | | |
|---|---|---|---|---|---|---|---|
| Species | No. ATCC | Medium | $10^6$ | $10^5$ | $10^4$ | $10^3$ | $10^2$ |
| _B. cereus_ | 11778 | SMA-BC | + (Blue) | + (Blue) | + (Blue) | 5 (Blue) | 1 (Blue) |
| | | TSA-BC | + (Blue) | + (Blue) | + (Blue) | 2 (Blue) | – |

Legend: Number of colonies (colony color)
+ Growth positive
– Non-growth

Test Example 2: Growth Test

[Preparation of Medium]

The medium (N-BC medium) of the present invention was obtained as follows. A hydroxypropyl cellulose (HPC) solution of the composition shown in Table 5 was added in a mixture of the medium composition shown in Table 4, the mixture was suspended in the HPC solution while stirring, then 0.9 mL of the obtained suspension was aliquoted into two containers (50Φ mm) each housing a cotton sheet (50Φ mm), and the resultant two containers were stacked in two stages, gradually dried overnight in a non-open space, and then covered. The medium was hermetically packaged in an aluminum packaging material together with a desiccant, and then sterilized with gamma irradiation with a surface dose of 10 to 20 kGy.

[Strain Under Test]

As the strain under test, a strain precultured for 24 hours in TSA was used, the precultured strain was adjusted by using a sterilized saline solution so that a bacterial liquid at $1 \times 10^1$ to $1 \times 10^4$ cfu/mL was obtained, and the bacterial liquid was inoculated into N-BC media by 1 mL each.

[Culture Results]

As shown in Table 6, when each strain was subjected to a test and cultured at 30° C. for 24 hours, favorable growth and development of blue color of _B. cereus_ were observed in the N-BC medium.

From the results, it was found that by combining a phosphatidylinositol-specific phospholipase C substrate having a detectable chromogenic free radical, such as X-IP with a β-lactam antibiotic such as aztreonam in addition to trimethoprim, the _Bacillus cereus_ can be favorably detected. It was also found that amphotericin B that is an antifungal agent may further be added.

TABLE 4

| No. | Raw material name | Composition |
|---|---|---|
| 1 | Casein peptone | 10 g |
| 2 | Meat extract | 5 g |
| 3 | Sodium chloride | 5 g |
| 4 | Mannitol | 10 g |
| 5 | Sodium pyruvate | 1 g |
| 6 | Trimethoprim* | 0.005 g |
| 7 | Amphotericin B* | 0.00117 g |

TABLE 4-continued

| No. | Raw material name | Composition |
|---|---|---|
| 8 | Aztreonam | 0.0005 g |
| 9 | X-IP | 0.6 g |
| 10 | Disodium hydrogen - phosphate anhydrous | 4 g |
| 11 | Sodium dihydrogen phosphate•anhydrous | 1 g |
| 12 | Xanthane gum | 45 g |
| 13 | Sodium carbonate, anhydrous | Correction amount |

*Added in only the composition of "+" in Table 6

TABLE 5

| No. | Raw material name | Composition |
|---|---|---|
| 1 | Hydroxypropyl cellulose | 1 g |
| 2 | Ethanol | 0.9 L |

TABLE 6

| | | | Amphotericin B | | | | + | + |
|---|---|---|---|---|---|---|---|---|
| | | | | | Trimethoprim | | | |
| | | | | | + | | | − |
| Determination | | | | | Bacterial concentration | | | |
| time | | | $10^4$ | $10^3$ | $10^2$ | $10^1$ | $10^4$ | $10^3$ |
| 24 hours | *B. cereus* | ATCC11778 | + (Blue) | + (Blue) | + (Blue) | 12 (Blue) | + (Blue) | + (Blue) |
| | *C. albicans* | ATCC14053 | − | − | − | − | − | − |
| | *C. albicans* | ATCC10231 | − | − | − | − | − | − |
| | *L. monocytogenes* | ATCC13932 | − | − | − | − | + (Blue) | + (Blue) |
| | *L. monocytogenes* | ATCC15313 | − | − | − | − | + (Blue) | + (Blue) |
| 72 hours | *B. cereus* | ATCC11778 | + (Blue) | + (Blue) | + (Blue) | 12 (Blue) | + (Blue) | + (Blue) |
| | *C. albicans* | ATCC14053 | + (Blue) | − | − | − | − | − |
| | *C. albicans* | ATCC10231 | + (Blue) | − | − | − | − | − |
| | *L. monocytogenes* | ATCC13932 | − | − | − | − | + (Blue) | + (Blue) |
| | *L. monocytogenes* | ATCC15313 | − | − | − | − | + (Blue) | + (Blue) |

| | | | Amphotericin B | | | | + | − |
|---|---|---|---|---|---|---|---|---|
| | | | | | Trimethoprim | | | |
| | | | | | − | | | + |
| Determination | | | | | Bacterial concentration | | | |
| time | | | $10^2$ | $10^1$ | $10^4$ | $10^3$ | $10^2$ | $10^1$ |
| 24 hours | *B. cereus* | ATCC11778 | 7 (Blue) | 14 (Blue) | + (Blue) | + (Blue) | + (Blue) | 11 (Blue) |
| | *C. albicans* | ATCC14053 | − | − | − | − | − | − |
| | *C. albicans* | ATCC10231 | − | − | − | − | − | − |
| | *L. monocytogenes* | ATCC13932 | + (Blue) | + (Blue) | − | − | − | − |
| | *L. monocytogenes* | ATCC15313 | + (Blue) | + (Blue) | − | − | − | − |
| 72 hours | *B. cereus* | ATCC11778 | 7 (Blue) | 14 (Blue) | + (Blue) | + (Blue) | + (Blue) | 11 (Blue) |
| | *C. albicans* | ATCC14053 | − | − | + (Blue) | + (Blue) | 40 (Blue) | 6 (Blue) |
| | *C. albicans* | ATCC10231 | − | − | + (Blue) | + (Blue) | 27 (Blue) | 6 (Blue) |
| | *L. monocytogenes* | ATCC13932 | + (Blue) | + (Blue) | − | − | − | − |
| | *L. monocytogenes* | ATCC15313 | + (Blue) | + (Blue) | − | − | − | − |

Legend: Number of colonies (colony color)
+ Growth positive
− Non-growth

Test Example 3: Multistrain Test (*Bacillus cereus* Group)

[Preparation of Medium]

The N-BC medium and the medium (EX-BC medium) disclosed in Patent Literature 1 were obtained as follows. A HPC solution shown in Table 5 was added in each of mixtures of the medium composition shown in Table 4 for the N-BC medium and the medium composition shown in Table 7 for the EX-BC medium, each mixture was suspended in the HPC solution while stirring, then 0.9 mL of the obtained suspension was aliquoted into two containers (50Φ mm) each housing a cotton sheet (50Φ mm), and the resultant two containers were stacked in two stages, gradually dried overnight in a non-open space, and then covered.

The media were each hermetically packaged in an aluminum packaging material together with a desiccant, and then sterilized with gamma irradiation with a surface dose of 10 to 20 kGy.

Further, as the control media, TSA, a MYP agar medium (MYP), and a NGKG agar medium (NGKG) were used.

[Strain Under Test]

As the strain under test, a strain precultured for 24 hours in TSA was used, the precultured strain was adjusted by using a sterilized saline solution so that a bacterial liquid at $1\times10^1$ to $1\times10^4$ cfu/mL was obtained. The bacterial liquid was inoculated into media by 1 mL each.

[Culture Results]

As shown in Table 8, each strain was subjected to a test and cultured at 30° C. for 22 hours, the concentration of inoculated bacteria was calculated from the number of grown colonies. In this case, only the EX-BC was cultured at 35° C. From the results, it was found that in the N-BC medium, any *B. cereus* has a growth performance equivalent to those in the TSA, the MYP and the NGKG.

TABLE 7

| No. | Raw material name | Composition |
|---|---|---|
| 1 | Casein peptone | 10 g |
| 2 | Meat peptone | 10 g |
| 3 | LAB LEMCO powder | 5 g |
| 4 | Sodium chloride | 5 g |
| 5 | Glycine | 10 g |

TABLE 7-continued

| No. | Raw material name | Composition |
|---|---|---|
| 6 | Mannitol | 10 g |
| 7 | Sodium pyruvate | 1 g |
| 8 | Trimethoprim | 0.005 g |
| 9 | Amphotericin B | 0.00117 g |
| 10 | Polymyxin B | 500,000 u |
| 11 | Lincomycin | 0.0025 g |
| 12 | 5-Bromo-4-chloro-3-indoxyl-α-D-glucopyranoside | 0.15 g |
| 13 | Xanthane gum | 2 0 g |
| 14 | Sodium carbonate, anhydrous | Correction amount |

TABLE 8

| Species | Bacterium No. | TSA 30° C. | MYP 30° C. | NGKG 30° C. | EX-BC medium 35° C. | N-BC medium 30° C. |
|---|---|---|---|---|---|---|
| *Bacillus cereus* | ATCC 11778 | 7.60 | 7.76 | 7.74 | 7.54 | 7.60 |
| *Bacillus cereus* | ATCC 14579 | 6.92 | 7.14 | 7.30 | 6.96 | 7.06 |
| *Bacillus cereus* | ATCC 19637 | 6.75 | 6.98 | 7.17 | 6.28 | 6.93 |
| *Bacillus cereus* | NS 10609 | 7.50 | 7.51 | 7.67 | 7.24 | 7.36 |
| *Bacillus cereus* | NS 10610 | 7.30 | 7.55 | 7.45 | 6.74 | 7.51 |
| *Bacillus cereus* | NS 9116 | 7.91 | 8.10 | 8.20 | 7.97 | 7.93 |
| *Bacillus cereus* | NS 5109 | 7.53 | 7.63 | 7.64 | 7.44 | 7.62 |
| *Bacillus cereus* | NS 5201 | 7.02 | 6.99 | 7.03 | 6.49 | 6.81 |
| *Bacillus cereus* | NS 5202 | 6.71 | 7.07 | 7.17 | 6.87 | 6.98 |
| *Bacillus cereus* | NS 5203 | 6.85 | 6.95 | 6.81 | 6.39 | 6.67 |
| *Bacillus cereus* | NS 5204 | 7.46 | 7.82 | 7.70 | 7.57 | 7.63 |
| *Bacillus cereus* | NS 5205 | 7.51 | 7.82 | 7.71 | 7.36 | 7.51 |
| *Bacillus cereus* | NS 5206 | 7.72 | 7.94 | 7.75 | 7.55 | 7.77 |
| *Bacillus cereus* | NS 5207 | 7.51 | 7.62 | 7.61 | 7.39 | 7.60 |
| *Bacillus cereus* | NS 5208 | 7.50 | 7.56 | 7.56 | 6.95 | 7.45 |
| *Bacillus thuringiensis* | NBRC 101235 | 7.51 | 7.59 | 7.91 | 7.26 | 7.45 |
| | Average | 7.33 | 7.50 | 7.53 | 7.12 | 7.37 |

(Unit: $Log_{10}$ cfu/mL)

Test Example 4: Concentration Change Test of Trimethoprim

[Preparation of Medium]

The N-BC medium was prepared in a similar manner to Test Example 2. In that case, the concentration of trimethoprim was changed so as to be 0, 0.1, 5.0, or 50 mg/L and the X-IP was changed so as to be 0.4 g/L, and then the test was conducted.

[Strain Under Test]

The strains shown in Table 9, which were each precultured for 24 hours in TSA, were used, each precultured strain was adjusted by using a sterilized saline solution so that a bacterial liquid at $1 \times 10^1$ to $1 \times 10^4$ cfu/mL was obtained. The bacterial liquid was inoculated into media by 1 mL each.

[Culture Results]

As shown in Table 9, in a case where the concentration of trimethoprim in the N-BC medium was set to 0 mg/L, the growth in each of the genus *Listeria* and the *Bacillus cereus* group was confirmed after culturing for 24 hours. In addition, in a case where the concentration of trimethoprim in the N-BC medium was set to 0.1 mg/L, 5 mg/L, or 50 mg/L, after culturing for 24 hours, the growth in the genus *Listeria* was suppressed, but meanwhile, the growth in the *Bacillus cereus* group was confirmed.

TABLE 9

| Species | Bacterium No. | Trimethoprim | $10^4$ | $10^3$ | $10^2$ | $10^1$ |
|---------|---------------|--------------|--------|--------|--------|--------|
| *Listeria ivanovii* | ATCC7681 | 0 mg | + | + | + | 84 |
| | | 0.1 mg | − | − | − | − |
| | | 5 mg | − | − | − | − |
| | | 50 mg | − | − | − | − |
| *Listeria monocytogenes* | ATCC13932 | 0 mg | + | + | + | 41 |
| | | 0.1 mg | − | − | − | − |
| | | 5 mg | − | − | − | − |
| | | 50 mg | − | − | − | − |
| *Listeria monocytogenes* | ATCC15313 | 0 mg | + | + | + | 128 |
| | | 0.1 mg | − | − | − | − |
| | | 5 mg | − | − | − | − |
| | | 50 mg | − | − | − | − |
| *Bacillus thuringiensis* | NBRC101235 | 0 mg | + | + | + | 8 |
| | | 0.1 mg | + | + | + | 6 |
| | | 5 mg | + | + | + | 6 |
| | | 50 mg | + | + | + | 8 |
| *Bacillus cereus* | ATCC19637 | 0 mg | + | + | 31 | 2 |
| | | 0.1 mg | + | + | 28 | 4 |
| | | 5 mg | + | + | 27 | 4 |
| | | 50 mg | + | + | 25 | 4 |
| *Bacillus cereus* | ATCC11778 | 0 mg | + | + | 47 | 4 |
| | | 0.1 mg | + | + | 44 | 4 |
| | | 5 mg | + | + | 43 | 6 |
| | | 50 mg | + | + | 33 | 3 |

Legend: Number of blue colonies (− Non-growth,

+ Growth positive)

Test Example 5: Multistrain Test (Non-*Bacillus cereus* Group)

[Preparation of Medium]

The N-BC medium and the EX-BC medium were prepared in a similar manner to Test Example 3.

[Strain Under Test]

As the strain under test, a strain precultured for 24 to 48 hours in TSA was used, the precultured strain was adjusted by using a sterilized saline solution so that a bacterial liquid at $1\times10^3$ to $1\times10^7$ cfu/mL was obtained. The bacterial liquid was inoculated into media by 1 mL each.

[Culture Results]

As shown in Table 10, when each strain was subjected to a test, the N-BC was cultured at 30° C. for 22 hours, and the EX-BC was cultured at 35° C. for 22 hours, and the growth of colony was confirmed. In the N-BC medium, development of blue color was confirmed in one strain of *Listeria monocytogenes*, however, false positive results of the genus *Corynebacterium*, the genus *Enterococcus*, and the genus *Staphylococcus*, which were observed in the EX-BC medium being a control medium, were no longer confirmed. Accordingly, it was found that there are fewer false positive results in the N-BC medium as compared with the EX-BC medium.

TABLE 10

| | | | 22 hours | | | | 48 hours | | | |
|---|---|---|---|---|---|---|---|---|---|---|
| | | | EX-BC medium | | N-BC medium | | EX-BC medium | | N-BC medium | |
| | Species | Bacterium No. (NS) | $10^7$ | $10^3$ | $10^7$ | $10^3$ | $10^7$ | $10^3$ | $10^7$ | $10^3$ |
| 1 | *Citrobacter amalonaticus* | 4272 | − | − | − | − | − | − | − | − |
| 2 | *Enterobacter aerogenes* | 4275 | − | − | − | − | − | − | − | − |
| 3 | *Enterobacter sakazakii* | 4278 | − | − | − | − | − | − | − | − |
| 4 | *Escherichia coli* | 8015 | − | − | − | − | − | − | − | − |
| 5 | *Escherichia hermannii* | 5684 | − | − | − | − | − | − | − | − |
| 6 | *Klebsiella ozaenae* | 4282 | − | − | − | − | − | − | − | − |
| 7 | *Klebsiella pneumonia* | 4280 | − | − | − | − | − | − | − | − |
| 8 | *Serratia rubidaeae* | 4735 | − | − | − | − | − | − | − | − |
| 9 | *Morganella morganii* | 4284 | − | − | − | − | − | − | − | − |
| 10 | *Proteus vulgaris* | 4286 | − | − | + (Yellow) | − | − | − | + (Yellow) | − |
| 11 | *Pseudomonas aeruginosa* | 4295 | − | − | + (White) | − | − | − | + (Green) | + (Green) |
| 12 | *Pseudomonas putida* | 4292 | − | − | − | − | − | − | − | − |
| 13 | *Acinetobacter calcoaceticus* | 4289 | − | − | − | − | − | − | − | − |
| 14 | *Corynebacterium minutissimum* | 3036 | − | − | − | − | + (White) | − | − | − |
| 15 | *Corynebacterium renale* | 3043 | − | − | − | − | − | − | − | − |
| 16 | *Corynebacterium xerosis* | 3037 | + (Blue) | − | − | − | + (Blue) | − | − | − |
| 17 | *Enterococcus avium* | 2999 | − | − | − | − | − | − | − | − |
| 18 | *Enterococcus durans* | 3002 | − | − | − | − | − | − | − | − |
| 19 | *Enterococcus faecalis* | 3019 | − | − | − | − | + (Blue) | − | − | − |
| 20 | *Enterococcus faecium* | 3020 | − | − | − | − | − | − | − | − |
| 21 | *Micrococcus luteus* | 7963 | − | − | − | − | − | − | − | − |
| 22 | *Staphylococcus aureus* | 3048 | − | − | − | − | − | − | − | − |
| 23 | *Staphylococcus auricularis* | 1841 | − | − | − | − | − | − | − | − |
| 24 | *Staphylococcus capitis* | 1836 | − | − | − | − | − | − | − | − |
| 25 | *Staphylococcus epidermidis* | 5845 | − | − | − | − | − | − | − | − |
| 26 | *Staphylococcus haemolyticus* | 1833 | − | − | − | − | − | − | − | − |
| 27 | *Staphylococcus hominis* | 1834 | − | − | − | − | − | − | − | − |
| 28 | *Staphylococcus lentus* | 1838 | − | − | − | − | − | + (White) | + (White) | + (White) |
| 29 | *Staphylococcus saprophyticus* | 1830 | − | − | − | − | − | − | − | − |
| 30 | *Staphylococcus sciuri* | 1839 | + (White) | − | − | − | + (Blue) | − | + (White) | − |
| 31 | *Staphylococcus simulans* | 1837 | − | − | − | − | − | − | + (White) | + (White) |
| 32 | *Staphylococcus warneri* | 1835 | − | − | − | − | + (Blue) | − | + (White) | + (White) |
| 33 | *Staphylococcus xylosus* | 1832 | + (Yellow) | − | − | − | + (Blue) | − | − | + (White) |
| 34 | *Leuconostoc mesenteroides* | 4931 | − | − | − | − | − | − | − | − |
| 35 | *Listeria monocytogenes* | 3045 | − | − | + (Blue) | − | − | − | + (Blue) | − |
| 36 | *Paenibacillus macerans* | 7655 | − | − | − | − | − | − | − | − |
| 37 | *Paenibacillus polymyxa* | 1102 | − | − | − | − | − | − | + (White) | − |
| 38 | *Clostridium perfringens* | 7379 | − | − | − | − | − | − | − | − |
| 39 | *Listeria innocua* | 3039 | − | − | − | − | − | − | − | − |
| 40 | *Listeria ivanovii* | 11131 | − | − | − | − | − | − | − | − |

TABLE 10-continued

| | | 22 hours | | | | 48 hours | | | |
| | | EX-BC medium | | N-BC medium | | EX-BC medium | | N-BC medium | |
| Species | Bacterium No. (NS) | $10^7$ | $10^3$ | $10^7$ | $10^3$ | $10^7$ | $10^3$ | $10^7$ | $10^3$ |
|---|---|---|---|---|---|---|---|---|---|
| 41 *Candida albicans* | 9488 | – | – | – | – | – | – | – | – |
| 42 *Saccharomyces cerevisiae* | 11226 | – | – | – | – | – | – | – | – |

Legend: Number of colonies (colony color)
+ Growth positive
– Non-growth
Blue: blue colored,
Green: green colored (by dyestuff produced by bacterial cells),
Yellow: yellow colored (by bacterial cells themselves), and
White: growth of uncolored

Test Example 6: Examination Using Food Material

[Preparation of Medium]

The N-BC medium, the EX-BC medium, and the MYP were each prepared in a similar manner to Test Example 3.

[Strain Under Test]

*B. cereus* ATCC 11778, ATCC14579, and ATCC19637 were each precultured for 24 hours in TSA, each precultured one was adjusted by using a sterilized saline solution so that a bacterial liquid at $1\times10^4$, $1\times10^6$, or $1\times10^8$ cfu/mL was obtained, and the bacterial liquid was added in 10 g of a predetermined food material by 0.1 mL each, and left to stand for 48 hours to 2 weeks at room temperature, in a cold state, or in a frozen state, and then, into each resultant material, 90 mL of sterilized saline solution was added to prepare a stomached food material sample liquid. One mL of the sample liquid was inoculated into the N-BC medium, the EX-BC medium, and the MYP.

[Culture Results]

Each strain was subjected to a test, and a strain in the N-BC and the MYP was cultured at 30° C. for 22 hours and a strain in the EX-BC was cultured at 35° C. for 22 hours, and then the number of bacteria grown in each medium was calculated. As shown in FIG. 1, the growth difference of the N-BC medium as compared with the MYP being a control medium was $1\times10^{-0.03}$ (MYP ratio 93%), whereas the growth difference of the EX-BC was $1\times10^{-0.49}$ (MYP ratio 32%), and thus, it was found that the growth is apparently improved.

Test Example 7: Colony-Forming Ability after Culturing for 22 Hours

[Preparation of Medium]

The N-BC medium and the EX-BC medium were prepared in a similar manner to Test Example 3.

[Strain Under Test]

*B. cereus* ATCC11778 precultured for 24 hours in TSA was used, the precultured strain was adjusted by using a sterilized saline solution so that a bacterial liquid at $1\times10^2$ cfu/mL was obtained. The bacterial liquid was inoculated into media by 1 mL each.

[Culture Results]

Figure 2:
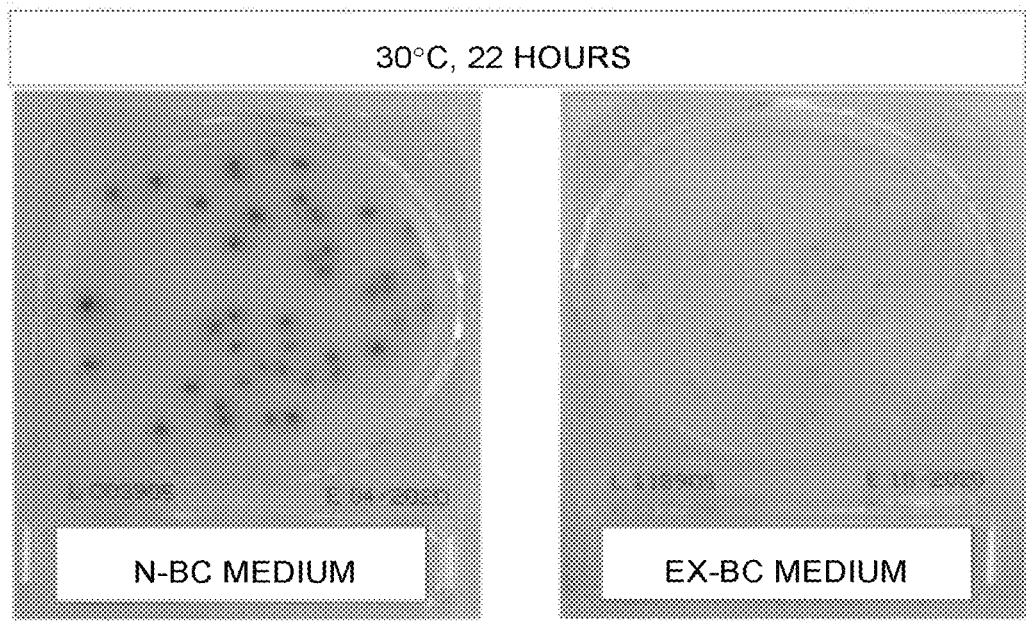
FIG. 2 is a diagram showing the states of colonies after culturing at 30° C. for 22 hours by using an N-BC medium and an EX-BC medium, respectively.

As shown in FIG. 2, when each strain was subjected to a test and was cultured at 30° C. for 22 hours, the growth of colony was confirmed. It was found that as compared with the EX-BC medium being a control medium, the growth of the N-BC medium is faster because the N-BC medium formed a larger colony.

Test Example 8: Comparison with Medium (US Medium) Disclosed in Patent Literature 2

[Preparation of Medium]

The medium composition of a US medium is shown in Table 11.

Preparation method: In a mixture weighed according to the medium composition shown in Nos. 1 to 10 of Table 11, 1 L of purified water was added, the mixture was dissolved in the purified water while heating at 121° C. for 15 minutes, and in the dissolved mixture, a mixture of the medium composition shown in Nos. 11 to 14 of Table 11 was added, then the obtained mixture was thoroughly stirred and aliquoted in a plastic Petri dish (90Φ mm) by 20 mL at a time, and the mixture in the dish was left to stand until being solidified to prepare a US medium. The N-BC medium was prepared in a similar manner to Test Example 2.

TABLE 11

| No. | Raw material name | Composition |
|---|---|---|
| 1 | Proteose peptone | 10.00 g |
| 2 | LAB LEMCO powder | 5.00 g |
| 3 | Yeast extract | 6.00 g |
| 4 | Sodium pyruvate | 10.00 g |
| 5 | Potassium phosphate (monobasic) | 0.24 g |
| 6 | Sodium phosphate (dibasic) | 2.50 g |
| 7 | Magnesium sulfate Anhydrous | 0.06 g |
| 8 | Cycloheximide | 0.20 g |
| 9 | Lithium chloride | 2.00 g |
| 10 | Agar | 15.00 g |
| 11 | Bovine Serum | 4.20 g |
| 12 | Ceftazidime | 0.001 g |
| 13 | X-IP | 0.35 g |
| 14 | Polymixin B sulfate | 0.013 g |

[Strain Under Test]

The strains shown in Table 12, which were each precultured for 24 hours in TSA, were used, each precultured strain was adjusted by using a sterilized saline solution so that a bacterial liquid at a specified concentration ($10^3$ to $10^7$ cfu/mL) was obtained. The bacterial liquid was inoculated into the US medium by 100 μL, and into the N-BC medium by 1 mL.

[Culture Results]

As shown in Table 12, when each strain was subjected to a test and cultured at 35° C. for 22 hours, in the US medium, a distinct colony with blue color was formed in the genus *Listeria*, and a distinct colony with white color was confirmed in the genus *Candida*. Meanwhile, when each strain was subjected to a test and cultured at 30° C. for 22 hours, in the N-BC medium, one strain of *Listeria monocytogenes* showed extremely weak blue color in the entire medium in the genus *Listeria*, however, a colony was not formed in the genus *Candida*.

TABLE 12

| Species | Bacterium No. | | US medium 35° C. | | N-BC medium 30° C. | |
|---|---|---|---|---|---|---|
| | | | $10^7$ | $10^4$ | $10^6$ | $10^3$ |
| *Listeria monocytogenes* | ATCC | 15313 | + (Blue) | + (Blue) | +w (Ultra-light blue) | – |
| *Listeria monocytogenes* | ATCC | 13932 | + (Blue) | + (Blue) | – | – |
| *Listeria ivanovii* | JCM | 7681 | + (Blue) | + (Blue) | – | – |
| *Listeria grayi* | ATCC | 19120 | + (White) | + (White) | – | – |
| *Listeria innocua* | ATCC | 33090 | + (White) | + (White) | – | – |
| *Listeria seeligeri* | ATCC | 35967 | + (White) | + (White) | – | – |
| *Listeria welshimeeri* | ATCC | 35897 | + (White) | + (White) | – | – |
| *Candida albicans* | ATCC | 14053 | + (White) | + (White) | – | – |
| *Candida albicans* | ATCC | 10231 | + (White) | + (White) | – | – |
| *Bacillus thuringiensis* | NBRC | 101235 | 94 (Blue) | 15 (Blue) | 106 (Blue) | 10 (Blue) |

Legend: Number of colonies (colony color)
+ Growth positive
+w Entire becomes light blue
– Non-growth

Test Example 9: Concentration of Amphotericin B

[Preparation of Medium]

The medium (N-BC medium) of the present invention was obtained as follows. A hydroxypropyl cellulose (HPC) solution of the composition shown in Table 5 was added in a mixture of the medium composition shown in Table 13, the mixture was suspended in the HPC solution while stirring, then 0.9 mL of the obtained suspension was aliquoted into two containers (50Φ mm) each housing a cotton sheet (50Φ mm), and the resultant two containers were stacked in two stages, gradually dried overnight in a non-open space, and then covered. The media were each hermetically packaged in an aluminum packaging material together with a desiccant, and then sterilized with gamma irradiation with a surface dose of 10 to 20 kGy. In that case, amphotericin B was adjusted with each medium so as to be 0 mg, 0.1 mg, 1 mg, and 10 mg.

TABLE 13

| No. | Raw material name | Composition | |
|---|---|---|---|
| 1 | Casein peptone | 10 | g |
| 2 | LAB LEMCO powder | 5 | g |
| 3 | Sodium chloride | 5 | g |
| 4 | Mannitol | 10 | g |
| 5 | Sodium pyruvate | 1 | g |
| 6 | Disodium hydrogen - phosphate anhydrous | 4 | g |

TABLE 13-continued

| No. | Raw material name | Composition | |
|---|---|---|---|
| 7 | Sodium dihydrogen phosphate•anhydrous | 1 | g |
| 8 | Trimethoprim | 5 | mg |
| 9 | Amphotericin B | 0, 0.1, 1, 10 | mg |
| 10 | Aztreonam | 0.5 | mg |
| 11 | X-IP | 0.4 | g |
| 12 | Xanthane gum | 45 | g |
| 13 | Sodium carbonate, anhydrous | Correction amount | |

[Strain Under Test]

As the strain under test, a strain precultured for 24 to 48 hours in TSA was used, the precultured strain was adjusted by using a sterilized saline solution so that a bacterial liquid at $1\times10^2$ to $1\times10^5$ cfu/mL was obtained. The bacterial liquid was inoculated into media by 1 mL each.

[Culture Results]

As shown in Table 14, when each strain was subjected to a test and was cultured at 30° C. for 24 to 44 hours, the growth of colony was confirmed. In the culture for 24 hours, in the N-BC medium, a colony with blue color was confirmed in three strains of *B. cereus* and *B. thuringiensis*, however, the growth was not observed in two strains of *C. albicans*. In addition, in a case of the culture for 44 hours, the results in three strains of *B. cereus* and *B. thuringiensis* were similar to those of the culture for 24 hours, however, in two strains of *C. albicans*, the growth or weak coloring was observed in a case of 0 mg or 0.1 mg of amphotericin B and a bacterial concentration of $10^5$ or $10^4$ cfu/mL.

TABLE 14

| Species | Bacterium No. | Amphotericin B | 24 hours | | | | 44 hours | | | |
|---|---|---|---|---|---|---|---|---|---|---|
| | | | $10^5$ | $10^4$ | $10^3$ | $10^2$ | $10^5$ | $10^4$ | $10^3$ | $10^2$ |
| *B. cereus* | ATCC11778 | 0 mg | + (Blue) | + (Blue) | + (Blue) | 37 (Blue) | + (Blue) | + (Blue) | + (Blue) | 37 (Blue) |
| *B. cereus* | ATCC19637 | | + (Blue) | + (Blue) | + (Blue) | 36 (Blue) | + (Blue) | + (Blue) | + (Blue) | + (Blue) |

TABLE 14-continued

| | | | 24 hours | | | | 44 hours | | | |
|---|---|---|---|---|---|---|---|---|---|---|
| Species | Bacterium No. | Amphotericin B | $10^5$ | $10^4$ | $10^3$ | $10^2$ | $10^5$ | $10^4$ | $10^3$ | $10^2$ |
| *B. thuringiensis* | NBRC101235 | | +<br>(Blue) | +<br>(Blue) | +<br>(Blue) | 51<br>(Blue) | +<br>(Blue) | +<br>(Blue) | +<br>(Blue) | 51<br>(Blue) |
| *C. albicans* | ATCC14053 | | – | – | – | – | +<br>(Blue) | w+<br>(Blue) | – | – |
| *C. albicans* | ATCC10231 | | – | – | – | – | +<br>(Blue) | w+<br>(Blue) | – | – |
| *B. cereus* | ATCC11778 | 0.1 mg | +<br>(Blue) | +<br>(Blue) | +<br>(Blue) | 37<br>(Blue) | +<br>(Blue) | +<br>(Blue) | +<br>(Blue) | 37<br>(Blue) |
| *B. cereus* | ATCC19637 | | +<br>(Blue) | +<br>(Blue) | +<br>(Blue) | 36<br>(Blue) | +<br>(Blue) | +<br>(Blue) | +<br>(Blue) | 36<br>(Blue) |
| *B. thuringiensis* | NBRC101235 | | +<br>(Blue) | +<br>(Blue) | +<br>(Blue) | 28<br>(Blue) | +<br>(Blue) | +<br>(Blue) | +<br>(Blue) | 28<br>(Blue) |
| *C. albicans* | ATCC14053 | | – | – | – | – | w+<br>(Blue) | – | – | – |
| *C. albicans* | ATCC10231 | | – | – | – | – | w+<br>(Blue) | – | – | – |
| *B. cereus* | ATCC11778 | 1.0 mg | +<br>(Blue) | +<br>(Blue) | +<br>(Blue) | 51<br>(Blue) | +<br>(Blue) | +<br>(Blue) | +<br>(Blue) | 51<br>(Blue) |
| *B. cereus* | ATCC19637 | | +<br>(Blue) | +<br>(Blue) | +<br>(Blue) | 35<br>(Blue) | +<br>(Blue) | +<br>(Blue) | +<br>(Blue) | 35<br>(Blue) |
| *B. thuringiensis* | NBRC101235 | | +<br>(Blue) | +<br>(Blue) | +<br>(Blue) | 39<br>(Blue) | +<br>(Blue) | +<br>(Blue) | +<br>(Blue) | 39<br>(Blue) |
| *C. albicans* | ATCC14053 | | – | – | – | – | – | – | – | – |
| *C. albicans* | ATCC10231 | | – | – | – | – | – | – | – | – |
| *B. cereus* | ATCC11778 | 10 mg | +<br>(Blue) | +<br>(Blue) | +<br>(Blue) | 49<br>(Blue) | +<br>(Blue) | +<br>(Blue) | +<br>(Blue) | 49<br>(Blue) |
| *B. cereus* | ATCC19637 | | +<br>(Blue) | +<br>(Blue) | +<br>(Blue) | 39<br>(Blue) | +<br>(Blue) | +<br>(Blue) | +<br>(Blue) | 39<br>(Blue) |
| *B. thuringiensis* | NBRC101235 | | +<br>(Blue) | +<br>(Blue) | +<br>(Blue) | 38<br>(Blue) | +<br>(Blue) | +<br>(Blue) | +<br>(Blue) | 38<br>(Blue) |
| *C. albicans* | ATCC14053 | | – | – | – | – | – | – | – | – |
| *C. albicans* | ATCC10231 | | – | – | – | – | – | – | – | – |

Legend: Number of colonies (colony color)
+ Growth positive
w+ Entire surface of medium was dyed light blue
– Non-growth

Test Example 10: Agar Medium

[Preparation of Medium]

The medium composition based on TSA is shown in Table 15.

Preparation method: In a mixture of the medium composition (excluding X-IP, aztreonam, and ceftazidime) shown in Table 15, 1 L of purified water was added, the mixture was dissolved in the purified water while heating at 121° C. for 15 minutes, then the obtained mixture was thoroughly stirred, and into the resultant mixture, X-IP, and aztreonam or ceftazidime as needed were added, then the obtained mixture was stirred and aliquoted in a plastic Petri dish (90Φ mm) by 20 mL at a time, and the mixture in the dish was left to stand until being solidified to prepare a TSA-BC.

TABLE 15

| No. | Raw material name | Composition |
|---|---|---|
| 1 | Peptone | 15.0 g |
| 2 | Soy peptone | 5.0 g |
| 3 | Sodium chloride | 5.0 g |

TABLE 15-continued

| No. | Raw material name | Composition |
|---|---|---|
| 4 | Agar | 15.0 g |
| 5 | X-IP | 0.4 g |
| 6 | Trimethoprim | 5 mg |
| 7 | Amphotericin B | 1.12 mg |
| 8 | Aztreonam or ceftazidime | 0, 0.05, 0.5, 5 mg |

[Strain Under Test]

Strains shown in Table 16 were precultured for 24 hours in TSA, each precultured strain was adjusted by using a sterilized saline solution so that a bacterial liquid at $1 \times 10^1$ to $1 \times 10^5$ cfu/mL was obtained, and the bacterial liquid was inoculated into media by 0.05 mL each.

[Culture Results]

As shown in Table 16, when each strain was subjected to a test and cultured at 30° C. for 22 hours, favorable growth and development of blue color of *B. cereus* were observed in the TSA-BC. However, by adding aztreonam or ceftazidime, the formation of a white colony was suppressed in *E. coli* or *E. amnigenus*.

TABLE 16

| Drug | Drug concentration | Bacterial name | Bacterium No. | $10^5$ | $10^4$ | $10^3$ | $10^2$ | $10^1$ |
|---|---|---|---|---|---|---|---|---|
| | Not contained | *B. cereus* | ATCC11778 | +<br>(Blue) | +<br>(Blue) | +<br>(Blue) | 16<br>(Blue) | 2<br>(Blue) |
| | | *B. cereus* | ATCC19637 | +<br>(Blue) | +<br>(Blue) | +<br>(Blue) | 5<br>(Blue) | – |

TABLE 16-continued

| Drug | Drug concentration | Bacterial name | Bacterium No. | $10^5$ | $10^4$ | $10^3$ | $10^2$ | $10^1$ |
|---|---|---|---|---|---|---|---|---|
| | | B. thuringiensis | NBRC101235 | + (Blue) | + (Blue) | + (Blue) | 15 (Blue) | 1 (Blue) |
| | | E. coli | ATCC8739 | 1 (White) | – | – | – | – |
| | | E. amnigenus | ATCC33072 | + (White) | 19 (White) | 1 (White) | – | – |
| Aztreonam | 0.05 mg | B. cereus | ATCC11778 | + (Blue) | + (Blue) | + (Blue) | 13 (Blue) | 1 (Blue) |
| | | B. cereus | ATCC19637 | + (Blue) | + (Blue) | + (Blue) | 2 (Blue) | 3 (Blue) |
| | | B. thuringiensis | NBRC101235 | + (Blue) | + (Blue) | + (Blue) | 16 (Blue) | 3 (Blue) |
| | | E. coli | ATCC8739 | – | – | – | – | – |
| | | E. amnigenus | ATCC33072 | 2 (White) | – | – | – | – |
| | 0.5 mg | B. cereus | ATCC11778 | + (Blue) | + (Blue) | + (Blue) | 12 (Blue) | 1 (Blue) |
| | | B. cereus | ATCC19637 | + (Blue) | + (Blue) | + (Blue) | 10 (Blue) | 1 (Blue) |
| | | B. thuringiensis | NBRC101235 | + (Blue) | + (Blue) | + (Blue) | 13 (Blue) | 1 (Blue) |
| | | E. coli | ATCC8739 | – | – | – | – | – |
| | | E. amnigenus | ATCC33072 | – | – | – | – | – |
| | 5 mg | B. cereus | ATCC11778 | + (Blue) | + (Blue) | + (Blue) | 17 (Blue) | 2 (Blue) |
| | | B. cereus | ATCC19637 | + (Blue) | + (Blue) | + (Blue) | 5 (Blue) | 1 (Blue) |
| | | B. thuringiensis | NBRC101235 | + (Blue) | + (Blue) | + (Blue) | 16 (Blue) | 2 (Blue) |
| | | E. coli | ATCC8739 | – | – | – | – | – |
| | | E. amnigenus | ATCC33072 | – | – | – | – | – |
| Ceftazidime | 0.05 mg | B. cereus | ATCC11778 | + (Blue) | + (Blue) | + (Blue) | 11 (Blue) | 2 (Blue) |
| | | B. cereus | ATCC19637 | + (Blue) | + (Blue) | + (Blue) | 7 (Blue) | – |
| | | B. thuringiensis | NBRC101235 | + (Blue) | + (Blue) | + (Blue) | 13 (Blue) | 5 (Blue) |
| | | E. coli | ATCC8739 | – | – | – | – | – |
| | | E. amnigenus | ATCC33072 | + (White) | 33 (White) | 1 (White) | – | – |
| | 0.5 mg | B. cereus | ATCC11778 | + (Blue) | + (Blue) | + (Blue) | 13 (Blue) | – |
| | | B. cereus | ATCC19637 | + (Blue) | + (Blue) | + (Blue) | 12 (Blue) | – |
| | | B. thuringiensis | NBRC101235 | + (Blue) | + (Blue) | + (Blue) | 10 (Blue) | 3 (Blue) |
| | | E. coli | ATCC8739 | – | – | – | – | – |
| | | E. amnigenus | ATCC33072 | – | – | – | – | – |
| | 5 mg | B. cereus | ATCC11778 | + (Blue) | + (Blue) | + (Blue) | 17 (Blue) | – |
| | | B. cereus | ATCC19637 | + (Blue) | + (Blue) | + (Blue) | 5 (Blue) | 3 (Blue) |
| | | B. thuringiensis | NBRC101235 | + (Blue) | + (Blue) | + (Blue) | 16 (Blue) | 4 (Blue) |
| | | E. coli | ATCC8739 | – | – | – | – | – |
| | | E. amnigenus | ATCC33072 | – | – | – | – | – |

Legend: Number of colonies (colony color)
+ Growth positive
– Non-growth

From the above, by using the medium of the present invention, the presence or absence of a *Bacillus cereus* group in a test sample can be accurately efficiently and easily discriminated. Further, the medium is inexpensive, and was simply and easily prepared. Therefore, the medium can be widely used for inspection of, for example, general foods and beverages, and water, and for inspection of production process.

The invention claimed is:

1. A medium for *Bacillus cereus* group detection, comprising, as concentrations at the time of detection:

from 0.001 to 10 g/l of a phosphatidylinositol-specific phospholipase C substrate having a detectable chromogenic or fluorescent free radical;

from 0.01 to 500 mg/l of trimethoprim;

from 0.001 to 100 mg/l of a cephem antibiotic or a monobactam antibiotic; and from 0.001 to 100 mg/l of a polyene antifungal agent, wherein the cephem antibiotic comprises ceftazidime, the monobactam antibiotic comprises aztreonam, and the polyene antifungal agent comprises amphotericin B, wherein the *Bacillus cereus* group is at least one bacterium selected from the group consisting of *Bacillus cereus*, *Bacillus anthracis*, *Bacillus thuringiensis*, *Bacillus mycoides*, *Bacillus pseudomycoides*, *Bacillus weihenstephanensis*, *Bacillus cytotoxicus*, and *Bacillus toyonensis*.

2. The medium for *Bacillus cereus* group detection according to claim 1, wherein the phosphatidylinositol-specific phospholipase C substrate having a detectable chromogenic or fluorescent free radical is at least one selected from the group consisting of 5-bromo-4-chloro-3-indoxyl myo-inositol-1-phosphate, 5-bromo-6-chloro-3-indoxyl myo-inositol-1-phosphate, 6-chloro-3-indoxyl myo-inositol-1-phosphate, 4-methylumbelliferone myo-inositol 1-phosphate, 4-nitrophenyl-myo-inositol-1-phosphate, luciferin-myo-inositol-1-phosphate, and a salt thereof.

3. A method for detecting a *Bacillus cereus* group, comprising:

inoculating a sample into the medium of claim 1 to culture the sample; and determining a detectable colony on the medium.

\* \* \* \* \*